United States Patent [19]

Leung et al.

[11] Patent Number: 5,585,465
[45] Date of Patent: Dec. 17, 1996

[54] ISOLATED TOXIN ASSOCIATED WITH KAWASAKI SYNDROME

[75] Inventors: Donald Leung, Englewood, Colo.; Patrick Schlievert, Edina, Minn.; Cody Meissner, Arlington, Mass.

[73] Assignees: National Jewish Center for Immunology and Respiratory Medicine, Denver, Colo.; New England Medical Center Hospital, Inc., Boston, Mass.; Regents of the University of Minnesota, Minneapolis, Minn.

[21] Appl. No.: 440,221

[22] Filed: May 12, 1995

Related U.S. Application Data

[60] Division of Ser. No. 190,653, Jan. 28, 1994, abandoned, which is a continuation-in-part of Ser. No. 152,456, Nov. 12, 1993, Pat. No. 5,476,767, which is a continuation-in-part of Ser. No. 42,731, Apr. 5, 1993, Pat. No. 5,470,716.

[51] Int. Cl.$^6$ ............................................. C07K 14/31
[52] U.S. Cl. ................................... 530/350; 530/820
[58] Field of Search .................................. 530/350, 820

[56] References Cited

U.S. PATENT DOCUMENTS 4,731,245  3/1988  Tsurumizu et al. .................. 424/92
5,075,236  12/1991  Yone et al. ........................ 436/518

FOREIGN PATENT DOCUMENTS 9110680  7/1991  WIPO .

OTHER PUBLICATIONS

Schlievert, "Role of Superantigens in Human Disease", J. Infect. Dis. 167: 997–1002 (1993).

Miethke et al., "Pathogenesis of the toxic shock syndrome: T cell mediated lethal shock caused by the superantigen TSST–1", Eur. J. Immunol. 23: 1494–1500 (1993).

Abe et al., "Selective expansion of T cells expressly T–cell receptor variable regions V$\beta$2 and B$\beta$8 in Kawasaki disease", Proc. Natl. Acad. Sci. USA 89: 4066–4070 (May 1992).

Schulman et al., "Management of Kawasaki syndrome: a concensus statement prepared by North American participants of the Third international Kawasaki Disease Symposium, Tokyo, Japan, Dec. 1988", Pediatr. Infect. Dis. J. 8: 663–665 (1989).

Barsumian et al., "Heterogeneity of Group A Streptococcal Pyrogenic Endotoxin Type B", Infect. & Immunol. 20(2): 512–58 (May 1978).

Leung et al., "Endothelial Cell Activation and High Interleukin–1 Secretion In The Pathogenesis of Acute Kawasaki Disease", Lancer (Dec. 2, 1989), pp. 1289–1303.

Sheagren, "*Staphylococcus aureus* The Persistent Pathogen", N. Eng. J. Med. 310(21): 1368–1372 (May 24, 1984).

Schlievert et al., "Production of Staphylococcal Pyrogenic Exotoxin Type C: Influence of Physical and Chemical Factors", J. Infect. Dis. 147(2): 236–242 (Feb. 1983).

Schlievert et al., "Purification and Physicochemical and Biological Characterization of a Staphylococcal Pyrogenic Exotoxin", Infect. & Immunol. 23(3): 609–617 (Mar. 1979).

Lee et al., "Nucleotide Sequences and Biological Properties of Toxic Shock Syndrome toxin 1 From Ovine—and Bovine Associated *Staphylococcal aureus*", J. Infect. Dis. 165: 1056–1063 (1992).

Blomster–Hawtoma et al., "The Nucleotide and Partial Amino Acid Sequence of Toxic Shock Syndrome", J. Biol. Chem. 261: 15783–15786 (1986).

*Primary Examiner*—Chhaya D. Sayala
*Attorney, Agent, or Firm*—Felfe & Lynch

[57] ABSTRACT

The invention relates to the isolated toxin associated with Kawasaki syndrome and the bacteria from which these are isolated.

3 Claims, No Drawings

ISOLATED TOXIN ASSOCIATED WITH KAWASAKI SYNDROME

The invention described herein was developed in part under NIH censorship (ML37260). The U.S. government may therefore have certain rights in the invention.

RELATED APPLICATIONS

This application is a Divisional of Ser. No. 08/190,653 filed Jan. 28, 1994 abandoned which is a continuation-in-part of Ser. No. 08/152,456 filed Nov. 12, 1993, now U.S. Pat. No. 5,476,767, which is a continuation-in-part of application Ser. No. 08/042,731 filed Apr. 5, 1993 now U.S. Pat. No. 5,470,716.

FIELD OF THE INVENTION

This invention relates generally to Kawasaki syndrome, which is also known as mucocutaneous lymph node syndrome, or Kawasaki Disease. More particularly, it relates to nucleic acid molecules which code for the toxin associated therewith, as well as ramifications arising from its isolation.

BACKGROUND AND PRIOR ART

Kawasaki syndrome ("KS" hereafter) is an acute multi system vasculitis of unknown etiology. The disease primarily affects infants and young children, i.e., aged sixteen or younger. See Kawasaki, Jpn. J. Allergol 16: 178–222 (1967); Rauch et al., Pediatr. Infect. Dis. 4: 702-702 (1985). While KS does occur worldwide, it is most prevalent in Japan and in children of Japanese ancestry. Primary clinical manifestations include prolonged fever, bilateral non-exudative conjuctivitis, induration and erythema of extremities, inflammation of lips and oropharynx, polymorphous skin rash, and cervical lymphadenopathy. These indications are used in a clinical diagnosis of KS.

In Japan and in the United States, KS has become one of the most common causes of acquired heart disease in children. Recent studies have shown that when gamma globulin is administered intravenously ("IVGG") during the acute phase of the disease, coronary artery lesions, which otherwise develop in 15–25% of patients, are significantly decreased. See Newburger et al., N. Engl. J. Med. 315: 341-6 (1986); Nagashima et al., J. Pediatr. 110: 710-2 (1987); Firisho et al., Lancet ii: 1055-57 (1984); Rowley et al., J. Pediatr. 113: 290-94 (1988); Newburger et al., N. Eng. J. Med. 324: 1633-39 (1991). Thus, in order to treat this disease effectively, as with all other vasculitic diseases, early recognition is essential.

KS is characterized by an acute stage, as well as a convalescent stage. The acute phase is characterized, inter alia, by marked immune activation. Investigators have demonstrated, for example, increased number of circulating and infiltrating T cells bearing the HLA-DR activation antigen and elevated serum soluble IL-2 receptor levels. These phenomena are indicative of T-cell activation. See Leung et al., J. Clin. Invest. 79: 468–472 (1987); Terai et al., Hum. Pathol. 21: 231–234 (1990); Lang et al., J. Pediatr. 116: 592–596 (1990). In addition, acute KS has been associated with increased production of IL-1B, TNF-α, IL-6, IL-2, and IFN-γ. See, e.g., Matsubara et al., Clin. Immunol. Immunopathol 56: 29–36 (1990); Maury et al., J. Lab. Clin. Med. 113: 651-54 (1989); Lang et al., J. Pediatr. 115: 939-43 (1989); Leung et al., Lancet ii: 1928-1302 (1989); Rowley et al., Ped. Inf. Dis. J. 7: 663-67 (1988); Ueno et al., Clin. Exp. Immunol 76: 337–342 (1989); Jordan et al., in Kawasaki, ed., The Third International Kawasaki Disease Symposium 1989: 144-46. The cytokines referred to supra are believed to play a significant role in the pathogenesis of vascular cell injury during acute KS, due to their proinflammatory and prothrombotic effect on endothelial cells. See Mantovani et al., Immunol. Today 10: 370-74 (1989). Vascular endothelium, in KS lesions, has been demonstrated to express cytokine inducible leukocyte adhesion molecules known to be involved in localization of inflammatory cells. See Leung, supra. Patients with acute KS have been found to have cytotoxic antibodies against IL-1B, TNF-α and IFN-γ stimulated endothelial cells, but not unstimulated cells. See Leung et al., J. Clin. Invest. 77: 1428-35 (1986); Leung et al., J. Exp. Med. 164: 1958-72 (1986).

While epidemiologic studies directed toward identifying potential environmental toxins, and laboratory culturing of body fluids for known microbial agents have taken place, an etiological agent for KS has not been found. See Rauch et al., Ped. Infect. Dis. J. 6: 1016-21 (1987). Due to the acute, self-limited nature of the disease, geographic clustering of outbreaks, clinical symptoms of fever and eruptions which mimic conditions and diseases such as measles, roseola, and scarlet fever, as well as the unique susceptibility of young children, it has been suggested that humoral immunity to this organism develops early in life. KS is rarely seen over the age of 8 suggesting that there is an asymptomatic infection caused by a ubiquitous agent, followed by development of protective immunity in the general population.

The general observations on KS, suggest that this disease has some similarities with disorders characterized by response to a so-called "superantigen". The previously cited references show that various superantigens lead to expanded populations of Vβ elements or TCRs ("T cell receptor molecules"). This evidence is also presented in, e.g., Choi et al., J. Exp. Med. 172: 981-84 (1990); Kappler et al., Science 24: 811-13 (1989); and Choi et al, Proc. Natl. Acad. Sci. 86: 8941-45 (1989). The disclosures of these three references are all incorporated by reference herein. The superantigens, including bacterial toxins, provoke marked activation of T cells and monocytes/macrophages. For example, staphylococcal enterotoxins and streptococcal erythrogenic toxins induce IL-1 and TNF-α from monocytes. Staphylococcal enterotoxin and SPE-mediated stimulation of monocytes is a consequence of binding and transducing a positive signal through MHC-II molecules on monocyte cell surfaces. In the presence of antigen presenting cells, superantigens stimulate T-cell proliferation by selective stimulation of T cells expressing particular Vβ elements. For example, Staphylococcal TSST-1 stimulates T cells presenting Vβ2. Choi et al., J. Exp. Med. 172: 981-4 (1990), have shown expansion of Vβ2 cells in toxic shock syndrome. The similarities thus suggest at this time that vasculitic diseases especially KS, may involve the same phenomena as is involved in superantigen caused diseases and conditions, but, as noted supra, this is a theory rather than a known mechanism, as compared to the expansion of the Vβ subtype, which is an empirical phenomenon.

Abe et al., Proc. Natl. Acad. Sci. USA 89: 4066–4070 (5/92), the disclosure of which is incorporated by reference in its entirety, describe experiments wherein the T cell repertoire of patients with KS were studied. It was found that the variable regions Vβ2 and, to a lesser extent, Vβ8, were expanded within these patients, relative to controls and to other variable regions. The paper reiterates the discussion supra, i.e., that the cause of KS is unknown. The paper speculates that streptococcal exotoxins or homologous exotoxins may be involved in the pathogenesis of acute KS.

The parent of the subject application disclosed that a diagnosis of Kawasaki Syndrome can be made by assaying for Streptococcal bacteria, and its associated antigens, or by assaying for Staphyloccal bacteria which produce toxic shock syndrome toxin "TSST-1". More precisely, a strain of S. aureus which differs from all other previously observed strains has been identified. The implicated strain is a white color in appearance. It was observed that the cultures appeared benign, but were involved in pathological conditions. The observations suggested that other undiagnosed disorders in addition to KS may be associated with pathogenic bacteria which appear to be normal.

The present invention involves the isolation of a nucleic acid molecule which codes for a toxin associated with Kawasaki Syndrome. The toxin has a particular amino acid sequence, which is set forth, in SEQ ID NO: 1. The invention involves isolated nucleic acid molecules which code for proteins having the nucleotide sequence, set forth in SEQ ID NO: 2. Also disclosed are such nucleic acid molecules. Other features of the invention include vectors which comprise the nucleic acid molecules of the invention operably linked to promoters, as well as cell lines, such as prokaryotic (e.g., E. coli) and eukaryotic (e.g., CHO and COS) cells transfected with the nucleic acid molecule or with the promoters of the invention. The identification of the molecule and its coding sequence also enables the artisan to identify organisms implicated in Kawasaki Syndrome, by the use of specific probes.

BRIEF DESCRIPTION OF THE FIGURES

FIG. 1 is a Southern Blot of isolates from patients with Kawasaki Syndrome, compared to controls.

FIG. 2 is a Western Blot of isolates using anti-TSST antibodies.

DETAILED DESCRIPTION OF PREFERRED EMBODIMENTS

Example 1

Cultures were obtained from the pharynx, axilla, groin and rectum of sixteen patients with untreated, acute KS, and fifteen disease controls with fever and/or rash. The cultures were taken from all patients within 10 days of the onset of illness, and prior to initiation of intravenous gammaglobulin therapy. The criteria for diagnosing a subject as having acute KS were those of the American Heart Association Committee on Rheumatic Fever, JAMA 44: 1218–1219 (1990). Cultures were obtained using cotton swabs at all four of the sites given above, and were then incubated overnight at 37° C. Swabs from all sites were cultured on sheep blood agar plates, while swabs from the groin and rectum were also cultured on phenylethyl alcohol sheep blood agar. Both culture methodologies represent well known techniques. Bacterial cultures were identified, and all staphylococci and beta hemolytic streptococci isolated were screened for secretion of toxins by serial dilution double immunodiffusion, in accordance with Schlievert et al., J. Infect. Dis. 147: 236–242 (1983), the disclosure of which is incorporated by reference in its entirety.

When the cultures were analyzed, thirteen were found to have produced toxins associated with Vβ2 expressing T cells, i.e., toxic shock syndrome toxin-1 ("TSST-1") and streptococcal pyrogenic exotoxins B and C. (Choi et al., J. Exp. Med. 172: 981–984 (1990), Abe et al., J. Immunol. 146: 3747–3750 (1991); Tomai et al., Infect. Immun. 60: 701–705 (1992); Drake et al., J. Clin. Immunol. 12: 149–162 (1992)). In contrast, only one disease control produced any of these toxins, and in this isolated case, the causative organism was not the newly identified *S. aureus* strain which is a feature of this invention.

The bacteria found in these cultures were analyzed. Eleven of the thirteen positive cultures were found to contain a strain of *Staphylococcus aureus,* while the remaining two cultures were found to contain the streptococcal pyrogenic exotoxins (SPE) B and C.

Example 2

The bacteria isolated from the cultures were subjected to further examination. Each one produced 3.2 ug/ml of TSST-1, a quantity typical of most TSS associated *S. aureus.* All isolates were found to be tryptophan auxotrophs.

Of great interest were differences between the *S. aureus* of the KS cultures, and other *S aureus* strains. In particular, all KS isolates of *S. aureus* were white. In contrast, most strains of coagulase positive *S. aureus* are gold in color, as is implied by the name. This difference was also found between the KS isolates, those from a febrile control patient, those *S. aureus* isolated from skin infections, and those isolated from the vaginas of patients with toxic shock syndrome. Other assays using well recognized techniques show that the KS associated isolated were coagulase positive, and produced substantially less lipase, hemolysis, and protease than did the cultures from skin infections and toxic shock syndrome patients.

Table 1, which follows, summarizes the data on the subjects tested in Example 1. Table 2 summarizes the data on the bacterial isolates.

TABLE 1

Association of Kawasaki Syndrome with a white TSST-producing *S. aureus*

| | Kawasaki Syndrome Patients | Control Patients |
|---|---|---|
| Number of Patients | 16 | 15 |
| Sex (Male:Female) | 11:5 | 8:/ |
| Mean age in years (Range) | 5.5 (1–11) | 2.1 (1–5) |
| TSST-producing *S. aureus*-White | 11 | 0 |
| SPEB, SPEC producing Group A Streptococci | 2 | 0 |
| TSST-producing *S. aureus*-Gold | 0 | 1 |
| Normal Flora | 3 | 14 |

TABLE 2

Production of secreted virulence factors by isolates of *S. aureus.*

| Virulence Factor | Isotates of *Staph aureus* from: KS (11)[a] | Skin infections (10)[b] | Vaginal TSS (10) |
|---|---|---|---|
| TSST-1[c] | 3.2 | 0 | 3.2 |
| Pigment | White | Gold | Gold |
| Coagutase | Positive | Positive | Positive |
| Lipase[d] | 0.5 ± 0.4 | 3.2 ± 1.1 | 1.2 ± 0.8 |
| Homolysin[e] | 0.5 ± 0.3 | 52 ± 27 | 16 ± 4.4 |
| Protease[f] | 10 ± 6.3 | 29 ± 17 | 23 ± 11 |

[a]Numbers in parentheses are the number of isolates tested per group
[b]Wound, boil, abscess skin isolates
[c]TSST-1 μg/ml original culture fluid by serial dilution double immunodiffusion
[d]Lipase units/$10^8$ bacteria ± S.D. determined by hydrolysis of tributyrin
[e]Hemolysis units/$10^8$ bacteria ± S.D. determined by lysis of rabbit erythrocytes
[f]Protease units/$10^8$ bacteria ± S.D. determined by cleavage of casein The numbers in parenthesis indicate the number of samples tested. TSST-1 was determined as described supra, while both lipase and hemolysis are presented in units per $10^8$ bacteria, determined in accordance with Schlievert et al., Ann. Intern. Med. 96: 937–940 (1992), the disclosure of which is incorporated by reference. Protease is also presented in units per $10^8$ bacteria, in accordance with Hynes et al., J. Microbiol Meth. 4: 25–31 (1985).

Example 3

A set of experiments were carried out in which the DNA of the TSST-1 secreting *S. aureus* of the cultures was probed. The probe was the entire TSST-0 gene, i.e., tstO, described by Lee et al., J. Infect. Dis. 165: 1056–1063 (1992). This gene differs from gene tst which produces TSST-1, by only 14 nucleotides.

Samples were taken from all eleven positive cultures, together with control tryptophan ("H"), and tyrosine (4282) auxotrophs, as per Chu et al., Infect. Immun. 56: 2702–2708 (1988). All bacteria were cultured in Todd Hewitt broth. Chromosomal DNA was isolated after treatment with lysostaphin, following Chu et al., supra. The DNA samples were then digested with restriction endonuclease Cla1, the fragments were separated via electrophoresis through agarose, and then the DNA was transferred via Southern blotting to nitrocellulose, in accordance with the classic paper of Southern, J. Mol. Biol. 98: 503–517 (1975). All hybridization and detection were done by use of the Genius Kit of Boehringer Mannheim Corporation in accordance with manufacturer's instructions. The results are set forth in FIG. 1.

The Southern blot data confirmed a suspicion that the pathogenic strain has the tst gene integrated into the tryptophan operon, as per Chu et al., Infec. Immunol. 56: 2702–2708 (1988). This is typical of TSST-1 producing staphylococcus.

Example 4

A Western blot/immunoblot assay was carried out. To do this, isolated organisms were grown on sheep blood agar plates, as is described in Example 1. A disk of nitrocellulose paper was placed on top of the grown organisms, after which it was cultured for 24 hours on a blood agar plate. The disk was then removed, and the blotting procedure carried out. Specifically, the nitrocellulose was coated with 200 ml of 3% gelatin (3 g in 100 ml of TBS buffer: 0.02 M Tris, 0.5 M NaCl in 4 liters of $H_2O$, pH 7.5). This was then incubated for 30–45 minutes in 200 ml of 0.05% TBS/Tween (1 ml Tween/2 liters TBS), at 37° C. Following this, the nitrocellulose treated filter was with rabbit polyclonal anti-TSST at room temperature (25 ul), in 50 ml of TBS Tween. This was followed by washing twice for five minutes (each wash) in TBS/Tween, and then followed by incubation for 1% hours with conjugates of anti-rabbit immunoglobulin and alkaline phosphatase (25 ul per filter). This was followed by two washes in TBS/Tween, and two more washes in TBS, all for five minutes. Developing solution was then added (2 mg 5-bromo-4-Cl indolyl phosphate, 100 ul N,N-dimethyl formamide, 18 ml of barbital buffer (0.15 M, pH 9.2 in acetic acid), 2 ml of 0.1% nitroblue tetrazolium, and 40 ul of 2M $MgCl_2.6H_2O$).

The results, shown in FIG. 2, compare positive and negative controls to the Western blot work and confirm that the Western/Immunoblot methodology can be used to identify the microorganism of interest.

Example 5

The work described in example 3 supra was extended, and the *S. aureus* DNA identified in these experiments was sequenced, following standard techniques. One strain, isolated from a throat culture of a KS patient, was selected at random. The gene believed to be coding for "TSST-1" from this strain was sequenced. The nucleotide sequence with deduced amino acid sequence are presented in SEQ ID NO: 1. The gene codes for a protein of 234 amino acids, and when the stop codon TAA is added, is 705 bases long.

Comparison of the sequence with the known sequence for *S. aureus* TSST-1 reveals some interesting information. There are 5 bases which differ in the two sequences, at bases 326, 359, 360, 363, and 381. Two of these changes are "silent" with respect to the amino acid sequence (the changes at 363 and 381, which change the codons in which they appear from "ATC" and "GGC" to "ATT" and "GGT" respectively) The changes at 326, 359 and 360, however, are more meaningful, and result in a change from ACT (Thr) to ATT (Ile) and TAT (Tyr) to TGG (Trp) at amino acid positions 69 and 80, respectively. The amino acids which differ in the subject protein as compared to the normal TSST-1 molecule correspond to analogous amino acids in the ovine sequence homologous to TSST-1, as disclosed by Lee et al., J. Infect. Dis 165: 1056-63 (1992), the disclosure of which is incorporated by reference in its entirety. What is especially interesting is that the ovine homolog of TSST-1 has been shown to have biological properties which differ markedly from those of the TSST-1 molecule. Lee et al, supra, e.g., state in their abstract that "Like TSST-1, TSST-ovine was mitogenic, but unlike TSST-1, it was not pyrogenic, was unable to enhance endotoxic shock, and was unable to induce TSS in a rabbit model".

The data presented in examples 1–4 lead to several conclusions. The first conclusion is that the *S. aureus* isolates found in the KS samples are clonally derived. The second is that the virulence factors expressed by the organisms are such that they determine the host colonization niche. It had previously been shown, by Musser et al., Proc. Natl. Acad. Sci. 87: 225–229 (1990), that the majority of TSS *S. aureus* isolates are tryptophan auxotrophs, which have been clonally derived. This conclusion was based on electrophoretic analysis of bacterial enzymes. Analysis of the foregoing examples shows that all of the KS isolates are tryptophan auxotrophs, and demonstrates the predicted Southern hybridization patterns of tryptophan auxotrophs. The isolates also share a variety of other phenotypic characteristics.

It has been suggested, by Schlievert et al., Ann. Intern. Med. 96: 937–940 (1982), that TSS positive isolates of *S. aureus* differ from other *S. aureus* isolates in that they not only produce TSST-1, but also other potential virulence factors in a pattern that predicts preferred site of attachment to the host. For example, TSS isolates from mucosal surfaces do not make as much lipase as isolates from penetrating skin infections (e.g., carbuncles). In skin infections, the production of lipase may be necessary for skin invasion. Such isolates also tend to cause highly inflammatory lesions, while TSS isolates from mucous membranes typically cause little, if any inflammation.

The KS isolates described, named "Kawasaki Syndrome I" herein most closely resemble *S. aureus* mutants lacking a functional accessory gene regulator (agr), the global regulator of virulence factor production in this strain (Recsel et al., Mol. Gen. Genet. 202: 58–61 (1986)). Like the KS isolates, agr-mutants make only small amounts of lipase, hemolysin, and protease, and are white (Peng et al., J. Bacteriol 170: 4365–4372 (1989)). In contrast, however, agr mutants produce almost no TSST-1 (less than 0.1 ug/ml), in contrast to the amounts produced by the KS related isolates. Further, the KS isolates are not agr-mutants.

Prior studies have analyzed environmental conditions which control TSST-1 production by *S. aureus*. Schlievert et al., J. Infect. Dis. 147: 236–242 (1983); Todd et al., Infect. Immunol. 45: 339–344 (1984), and Kass et al., J. Infect. Dis. 158: 44–51 (1988), showed that animal protein, neutral pH, oxygen, and low environmental glucose are required for high levels of toxin production.

The foregoing examples provide a new method for diagnosing Kawasaki syndrome, or "KS". The methodology involves assaying a sample taken from a patient suspected of having KS, to determine at least one of (i) the presence of toxic shock syndrome toxin, (ii) the presence of white, toxic shock syndrome toxin producing S. aureus in the culture, (iii) Streptococcus exotoxin B or C, or (iv) Streptococcus which produce either of the recited strepexotoxins. Any of these "markers" are indicative of KS in the subject.

It is recognized that S. aureus, toxic shock syndrome toxin or streptococcus are also indicative of other conditions. Several points must be made in this regard, however. In general, the patient population associated with KS, i.e., children, especially children of oriental descent, especially Japanese, is not coextensive with the population prone to toxic shock syndrome. Further, as was pointed out, supra, KS is associated with several other diagnostic markers. Finally, in the case of the TSST-1 producing, white S. aureus bacteria associated with the disorder, all other pathological conditions where Staphylococcus is implicated involve standard, gold colored bacteria. Thus, white S. aureus is a specific marker for the disorder.

The manner in which the KS indicator is determined may vary, depending upon the wishes of the investigator. In the case of assays for toxins, immunoassays are preferred, such as the immunodiffusion assay discussed supra. Any standard immunoassay using anti-toxin polyclonal or monoclonal antibodies may be used, including immunoblots, ELISAs, RIAs, sandwich assays, and so forth. The targeted molecule may be TSST-1, SPE B, or SPE C.

If culturing of a sample for the bacteria is desired, the sample can be cultured in any of the standard media used for culturing bacteria, such as the blood agar media discussed supra. Visual inspection of the cultures for a white microorganism with phenotype and biochemical characteristics of S. aureus can then be carried out. Several of these characteristics are discussed supra, but others will be familiar to the skilled artisan and need not be set forth herein.

A specific strain of TSST-1 producing S. aureus which meets the criteria set forth herein, including the gene discussed in Example 5, referred to as "tst-KS" and cultured from samples taken from KS subjects was deposited at the American Type Culture Collection 12301 Parklawn Drive, Rockville, Md. 20852 on Jan. 5, 1994 and has been accorded Accession Number A.T.C.C. 55533. (S. aureus Kawasaki Syndrome 6). This culture can be used, e.g., as an immunogen for preparing strain specific antibodies, for nucleic acids to be used in probe assays, as well as for screening and/or development of potential therapeutic agents. Given the normal levels of toxin, but the low levels of other virulence factors, the organism is useful in further studies of the development of KS.

Example 5 describes the isolation and sequencing of the gene coding for a toxin associated with Kawasaki Syndrome. As is pointed out, supra the nucleic acid molecule differs from bases related sequences for TSST-1 and ovine-TSST. The differences at 326, 359, 360, 363, and 381, provides a methodology for screening for possible Kawasaki Syndrome. This method words on the standard assumption that the population pool for Kawasaki Syndrome is a limited one. Within this population, one may screen for Kawasaki Syndrome as compared to other pathological conditions, by assaying for the sequence discussed supra. Any of the standard nucleotide screening assays can be used, including but not being limited to polymerase chain reaction (PCR), and so forth. These methods are well known to the art, and need not be repeated here.

For example, KS can also be diagnosed via carrying out a nucleic acid based assay, such as Southern blotting. Other assays within this ambit include assaying with labelled probes, such as oligonucleotides which carry radiolabels, biotin, or other labels, polymerase chain reactions using oligonucleotides corresponding to the tst gene, and so forth.

The invention also contemplates systems for carrying out the assays, such as kits. In the case of DNA assays, for example, such kits include a support means for immobilizing the nucleic acids of the sample, such as nitrocellulose, and at least one probe for hybridizing to the target. Other optional buffers, hybridization solutions, e.g., SSC, wash buffers, and so forth may be included in the kit. Where immunoassays are involved, such kits may also contain a solid support, such as a membrane (e.g., nitrocellulose), a bead, sphere, test tube, rod, and so forth, to which a receptor such as an antibody or antibody fragment specific for the target molecule will bind. Such kits can also include a second receptor, such as a labelled antibody or labelled binding antibody fragment. Such kits can be used for sandwich assays to detect toxins or bacteria presenting the toxins. Kits for competitive assays are also envisioned. Such kits include, e.g., a solid phase to which a sample of the toxin to be detected is bound, as well as a portion of toxin specific antibody or antibody fragment. The binding receptor portion of such kits may be presented in a separate portion within the kit, or may be already bound to the solid, phase bound toxin. Such a system may be used in a displacement assay, e.g. In any such kit, the essentially elements are a moiety capable of detecting an agent indicative of KS, and a solid phase to which the agent binds, directly or indirectly.

The recognition that Streptococcus and S. aureus are associated with KS suggests various therapeutic methodologies for individuals with the condition. Staphylococcal infections are treated with a wide variety of drugs, antibiotics, etc., such as penicillin. The data disclosed herein lead to a therapeutic methodology, wherein a subject suffering from KS is administered an amount of an anti-Staphylococcal agent sufficient to treat the KS. In addition, the condition may be treated with anti-toxins rather than biocides effective against the organisms, as it is ultimately the toxins which are responsible for the condition. The invention does not include gammaglobulin therapy.

Other forms of therapy may also be provided, based upon the identification of an association between S. aureus TSST-1 and Kawasaki Syndrome. Key to any of these therapies is the ability to neutralize the TSST molecule, or to eliminate the strain. Either aim may be accomplished by modulating the immune response of the subject. This modulation may take one or more of several forms. For example, prevention of onset of Kawasaki Syndrome may be accomplished via administration of either mutated TSST-1 or mutated, non-pathogenic TSST-1 producing S. aureus, in a manner which elicits a protective immune response. This preventive modality may be utilized either to prevent initial onset of the syndrome, in a manner not unlike classical vaccination, or to prevent recurrence following treatment of the syndrome. TSST-1, as has been noted supra, has been identified as a superantigen. One may modify the superantigen, i.e., the TSST-1 molecule, so that it no longer provokes the toxic superantigen mediated T cell response, yet still provokes a protective immune response, including an antibody response to the toxin molecule. Further, derivatives or mutants of TSST-1 may be generated which interfere with the action of native TSST-1 via, e.g., binding to its receptors, and thus preventing the toxic consequences of this binding, and administered to subjects. Such TSST-1 competitors do not have the same effect as the normal molecule, and may be seen as being antagonists of TSST-1. Further derivatives can be used, when necessary, which in fact enhance the immune response of the subject to the toxin. Such an effect is desirable in individuals with KS who also have weakened or compromised immune systems. The materials which may be used include "modified" forms of TSST-1, as well as "mutated forms". The first term refers to molecules which contain a portion of the TSST-1 sequence as part of an unrelated molecule, whereas the latter refers to those materials where some fundamental change is made to TSST-1 itself (addition, substitution or deletion of amino acids, for example). Any of these materials may be used as vaccines, in the sense this term is generally used. Such vaccines may also include a number of other materials including adjuvants.

The therapy may also be accomplished via adoptive transfer or other immune stimulating approaches. Non-proliferative *S. aureus* organisms, cells transfected with the TSST-1 gene which present an antigen derived therefrom on their surface, but which are not viable, can also be used. Also envisioned are therapies based upon vectors, such as viral vectors containing nucleic acid sequences coding for the modified and mutated proteins described supra. These molecules, developed so that they do not per se provoke a pathological effect will stimulate the immune system to respond to the pathogenic *S. aureus*.

Other aspects of the invention will be evident to the skilled artisan, and need not be reiterated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated toxic shock syndrome toxin associated with Kawasaki syndrome consisting of the amino acid sequence of SEQ ID NO: 2.

2. The isolated and purified toxic shock syndrome toxin of claim 1 which differs from toxic shock syndrome toxin at amino acid residues 69 and 80.

3. The isolated and purified toxic shock syndrome toxin of claim 1 which is derived from a biologically pure culture of a strain of *Staphylococcus aureus,* A.T.C.C. 55533, which appears white when cultured.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 705 base pairs
        ( B ) TYPE: nucleic acids
        ( C ) STRANDEDNESS: single
        ( D ) TOPOLOGY: linear ( x i ) SEQUENCE DESCRIPTION: SEQ ID NO: 1:

| | | | | | | |
|---|---|---|---|---|---|---|
| ATGAATAAAA | AATTACTAAT | GAATTTTTTT | ATCGTAAGCC | CTTTGTTGCT | TGCGACAATC | 60 |
| GCTACAGATT | TTACCCCTGT | TCCCTTATCA | TCTAATCAAA | TAATCAAAAC | TGCAAAAGCA | 120 |
| TCTACAAACG | ATAATATAAA | GGATTTGCTA | GACTGGTATA | GTAGTGGGTC | TGACACTTTT | 180 |
| ACAAATAGTG | AAGTTTTAGA | TAATTCCTTA | GGATCTATGC | GTATAAAAAA | CACAGATGGC | 240 |
| AGCATCAGCC | TTATAATTTT | TCCGAGTCCT | TATTATAGCC | CTGCTTTTAC | AAAAGGGGAA | 300 |
| AAAGTTGACT | TAAACACAAA | AAGAATTAAA | AAAAGCCAAC | ATACTAGCGA | AGGAACTTGG | 360 |
| ATTCATTTCC | AAATAAGTGG | TGTTACAAAT | ACTGAAAAAT | TACCTACTCC | AATAGAACTA | 420 |
| CCTTTAAAAG | TTAAGGTTCA | TGGTAAAGAT | AGCCCCTTAA | AGTATTGGCC | AAAGTTCGAT | 480 |
| AAAAACAAT | TAGCTATATC | AACTTTAGAC | TTTGAAATTC | GTCATCAGCT | AACTCAAATA | 540 |
| CATGGATTAT | ATCGTTCAAG | CGATAAAACG | GGTGGTTATT | GGAAAATAAC | AATGAATGAC | 600 |
| GGATCCACAT | ATCAAAGTGA | TTTATCTAAA | AAGTTTGAAT | ACAATACTGA | AAAACCACCT | 660 |
| ATAAATATTG | ATGAAATAAA | AACTATAGAA | GCAGAAATTA | ATTAA | | 705 |

( 2 ) INFORMATION FOR SEQ ID NO: 2:

( i ) SEQUENCE CHARACTERISTICS:
        ( A ) LENGTH: 234 amino acid residues
        ( B ) TYPE: amino acids
        ( D ) TOPOLOGY: linear ( x i ) SEQUENCE DESCRIPTION: SEQ ID NO: 2:

| | | | | | | | | | | | | | | |
|---|---|---|---|---|---|---|---|---|---|---|---|---|---|---|
| Met | Asn | Lys | Lys | Leu 5 | Leu | Met | Asn | Phe | Phe 10 | Ile | Val | Ser | Pro | Leu 15 | Leu |
| Leu | Ala | Thr | Ile 20 | Ala | Thr | Asp | Phe | Thr 25 | Pro | Val | Pro | Leu | Ser 30 | Ser | Asn |
| Gln | Ile | Ile 35 | Lys | Thr | Ala | Lys | Ala 40 | Ser | Thr | Asn | Asp | Asn 45 | Ile | Lys | Asp |
| Leu | Leu 50 | Asp | Trp | Tyr | Ser | Ser 55 | Gly | Ser | Asp | Thr | Phe 60 | Thr | Asn | Ser | Glu |
| Val 65 | Leu | Asp | Asn | Ser | Leu 70 | Gly | Ser | Met | Arg | Ile 75 | Lys | Asn | Thr | Asp | Gly 80 |
| Ser | Ile | Ser | Leu | Ile 85 | Ile | Phe | Pro | Ser | Pro 90 | Tyr | Tyr | Ser | Pro | Ala 95 | Phe |
| Thr | Lys | Gly | Glu 100 | Lys | Val | Asp | Leu | Asn 105 | Thr | Lys | Arg | Ile | Lys 110 | Lys | Ser |
| Gln | His | Thr 115 | Ser | Glu | Gly | Thr | Trp 120 | Ile | His | Phe | Gln | Ile 125 | Ser | Gly | Val |
| Thr | Asn 130 | Thr | Glu | Lys | Leu | Pro 135 | Thr | Pro | Ile | Glu | Leu 140 | Pro | Leu | Lys | Val |
| Lys 145 | Val | His | Gly | Lys | Asp 150 | Ser | Pro | Leu | Lys | Tyr 155 | Trp | Pro | Lys | Phe | Asp 160 |
| Lys | Lys | Gln | Leu | Ala 165 | Ile | Ser | Thr | Leu | Asp 170 | Phe | Glu | Ile | Arg | His 175 | Gln |
| Leu | Thr | Gln | Ile 180 | His | Gly | Leu | Tyr | Arg 185 | Ser | Ser | Asp | Lys | Thr 190 | Gly | Gly |
| Tyr | Trp | Lys 195 | Ile | Thr | Met | Asn | Asp 200 | Gly | Ser | Thr | Tyr | Gln 205 | Ser | Asp | Leu |
| Ser | Lys 210 | Lys | Phe | Glu | Tyr | Asn 215 | Thr | Glu | Lys | Pro | Pro 220 | Ile | Asn | Ile | Asp |
| Glu 225 | Ile | Lys | Thr | Ile | Glu 230 | Ala | Glu | Ile | Asn | | | | | | |